United States Patent
Degen

(10) Patent No.: US 9,144,660 B2
(45) Date of Patent: Sep. 29, 2015

(54) IMPLANTABLE CATHETERS WITH STAGGERED SLITS, AND METHODS OF USING SAME

(71) Applicant: Sequana Medical AG, Zug (CH)

(72) Inventor: Thomas Degen, Bermensdorf (CH)

(73) Assignee: Sequana Medical AG, Zug (CH)

( * ) Notice: Subject to any disclaimer, the term of this patent is extended or adjusted under 35 U.S.C. 154(b) by 367 days.

(21) Appl. No.: 13/665,543

(22) Filed: Oct. 31, 2012

(65) Prior Publication Data

US 2014/0121590 A1 May 1, 2014

(51) Int. Cl.
*A61M 1/00* (2006.01)
*A61M 25/00* (2006.01)
*A61M 1/28* (2006.01)
*A61M 25/01* (2006.01)

(52) U.S. Cl.
CPC .............. *A61M 25/003* (2013.01); *A61M 1/285* (2013.01); *A61M 25/0071* (2013.01); *A61M 25/0108* (2013.01)

(58) Field of Classification Search
CPC ..................... A61M 25/0015; A61M 25/0071; A61M 2025/0188
USPC ............................................................ 604/29
See application file for complete search history.

(56) References Cited

U.S. PATENT DOCUMENTS

| | | |
|---|---|---|
| 4,398,910 A | 8/1983 | Blake et al. |
| 4,465,481 A * | 8/1984 | Blake ............................ 604/541 |
| D303,840 S | 10/1989 | Weilbacher |
| 5,593,394 A | 1/1997 | Kanesaka et al. |
| 5,676,670 A | 10/1997 | Kim |
| 5,713,864 A | 2/1998 | Verkaart |
| 6,099,513 A | 8/2000 | Spehalski |
| 6,146,354 A | 11/2000 | Beil |
| 6,478,789 B1 | 11/2002 | Spehalski et al. |
| 6,966,889 B2 | 11/2005 | Saab |
| 6,976,973 B1 | 12/2005 | Ruddell et al. |
| 6,986,752 B2 | 1/2006 | McGuckin et al. |
| D558,338 S | 12/2007 | Itoh |
| D558,341 S | 12/2007 | Fujiwara et al. |
| D558,342 S | 12/2007 | Fujiwara et al. |
| 7,311,690 B2 | 12/2007 | Burnett |
| 7,335,179 B2 | 2/2008 | Burnett |
| 8,202,248 B2 | 6/2012 | Burnett et al. |
| 8,398,577 B2 | 3/2013 | Burnett |
| 8,585,635 B2 | 11/2013 | Degen et al. |
| 2002/0091352 A1 | 7/2002 | McGuckin et al. |
| 2007/0208323 A1 | 9/2007 | Gregorich et al. |
| 2007/0233042 A1 | 10/2007 | Moehle et al. |
| 2009/0054874 A1 | 2/2009 | Barron et al. |
| 2012/0209165 A1 | 8/2012 | Degen et al. |
| 2013/0317476 A1 | 11/2013 | Searle et al. |
| 2014/0121590 A1 | 5/2014 | Degen |
| 2014/0213966 A1 | 7/2014 | Ostapoff et al. |

* cited by examiner

*Primary Examiner* — Kevin C Sirmons
*Assistant Examiner* — Deanna K Hall
(74) *Attorney, Agent, or Firm* — Foley & Lardner LLP; Christopher C. Bolten; Nicola A. Pisano

(57) ABSTRACT

Under one aspect of the present invention, a catheter includes an elongate member; a plurality of septa configured to define a plurality of lumens along the elongate member; and a plurality of slits defined through the elongate member, each slit configured to provide fluidic communication between an environment about the catheter and a corresponding lumen of the plurality of lumens, at least one slit having a different length than at least one other slit.

20 Claims, 16 Drawing Sheets

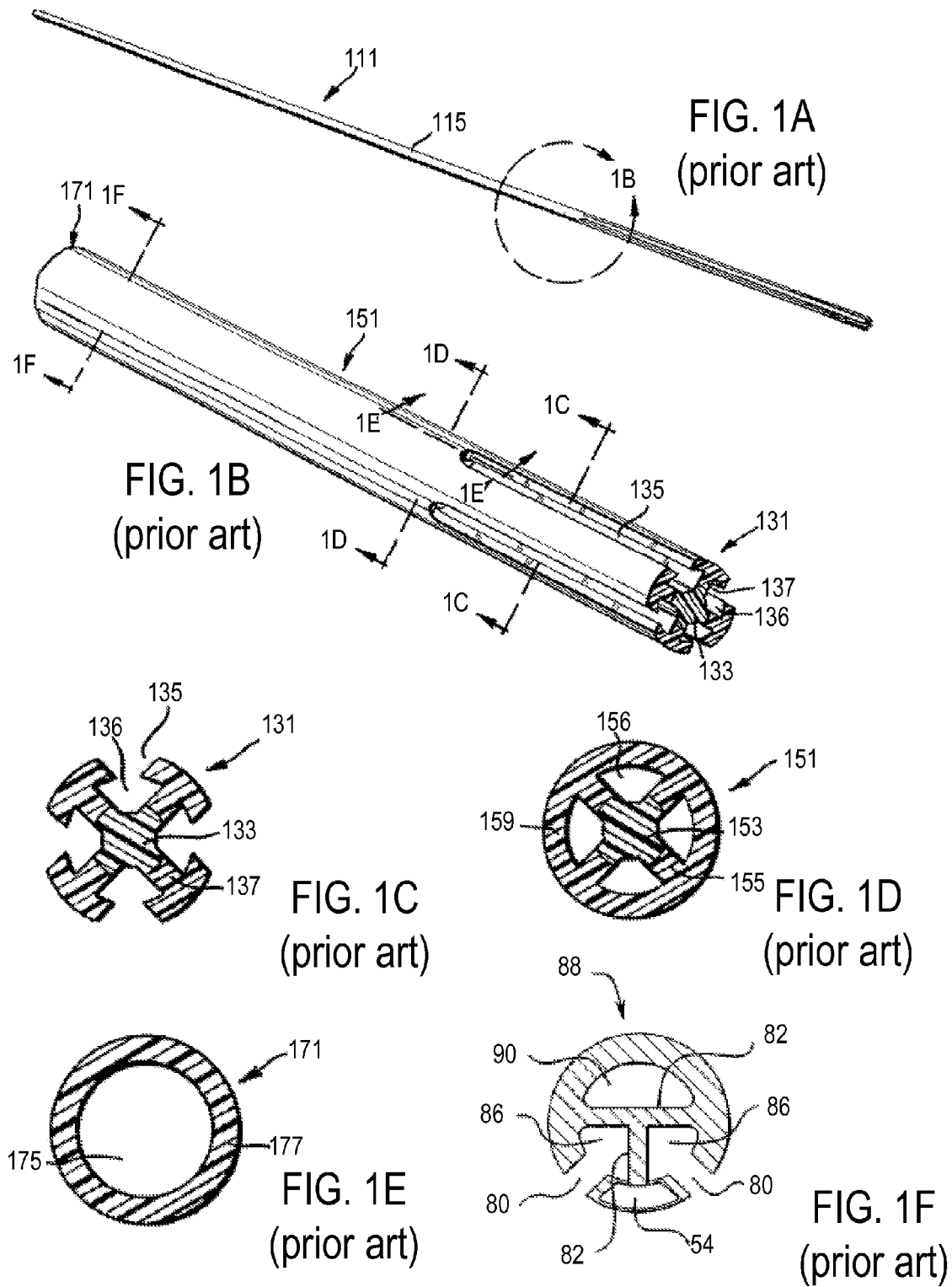

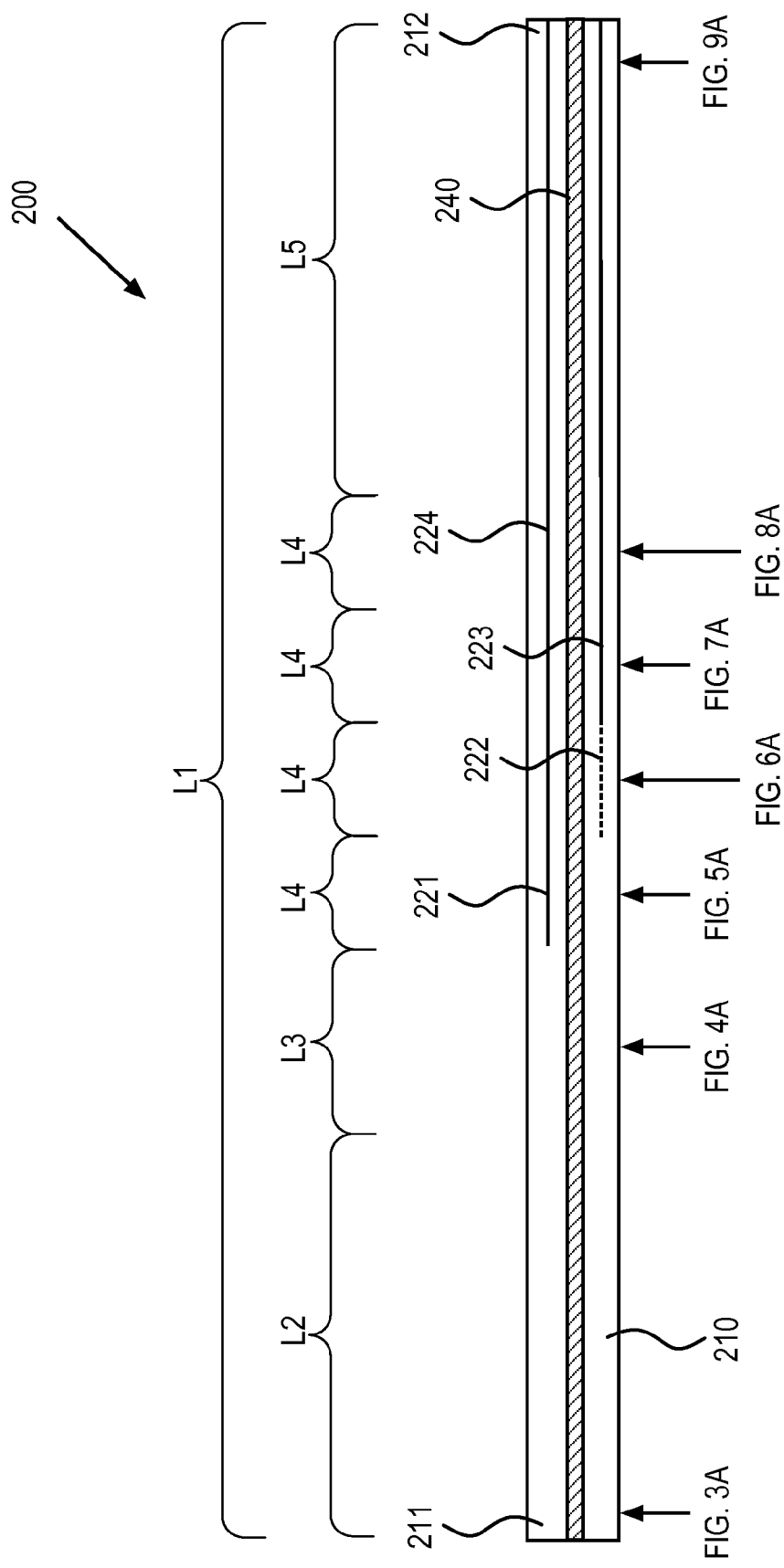

IMPLANTABLE CATHETERS WITH STAGGERED SLITS, AND METHODS OF USING SAME

FIELD OF INVENTION

This application generally relates to catheters, and methods of using the same.

BACKGROUND OF INVENTION

Fluid drainage catheters are known in the art. A class of catheters now commonly known as "Blake drains" were initially described in U.S. Pat. Nos. 4,398,910 and 4,465,481 to Blake et al., the entire contents of both of which are incorporated by reference herein. The Blake patents disclose wound drain catheters that include a flexible drain portion that is placed in a patient's body and in fluidic communication with a wound, and an outflow tube that exits the patient's body and connects to a suction device that draws fluid from the wound via the drain portion and the outflow tube. The Blake patents point to the deficiencies of perforated drain portions such as were previously known at that time, that included a length of tubing perforated by forming spaced apertures through the tubing wall. According to the Blake patents, one major problem with such perforated drains is that wound debris, such as clots, may block the apertures. Additionally, tissue may grow into the apertures, which not only may block the apertures, but also may make it difficult to remove the drain at a later time.

FIGS. 1A-1E, which have been adapted from U.S. Pat. No. 4,465,481, illustrate an exemplary embodiment of a "Blake drain" that includes longitudinal slits intended to overcome the deficiencies of perforated drains. Specifically, catheter 111 illustrated in perspective view in FIG. 1A, and in greater detail in 1B, includes a single continuous elongate member 115, which includes a drain segment 131, a second segment 151, called the transition tube segment, and a third segment 171, called the extension tube segment.

FIG. 1C illustrates a cross section of drain segment 131 along line 1C-1C in FIG. 1B. Drain segment 131 includes central core portion 133 with T-shaped members 137 projecting therefrom. T-shaped members 137 cooperate to define longitudinal flutes, lumens, or channels 136 that communicate with the environment surrounding the drain segment through grooves 135. FIG. 1D illustrates a cross section of transition tube segment 151 along line 1D-1D in FIG. 1B. Transition tube segment 151 includes core portion 153, which is colinear with core portion 133 of drain segment 131. Each of strut portions 155 projecting from core portion 153 is colinear with a corresponding T-shaped portion 137 of drain segment 131. The inner surface of tubular portion 159 is connected to the ends of the strut portions 155 so the tubular portion 159 and the strut portions 155 cooperate to form enclosed longitudinal channels 156. Each of the channels 156 communicates a corresponding lumen 136 of drain segment 131. FIG. 1E illustrates a cross section of extension tube segment 171 along line 1E-1E in FIG. 1B. Extension tube segment 171 includes tubular portion 177 defining internal longitudinal cavity 175. Tubular portion 177 is a continuation of tubular portion 159 so that cavity 175 communicates with all of the channels 156 of the transition tube segment 151.

As disclosed in U.S. Pat. No. 4,398,910, such a longitudinally fluted drain, rather than a perforated drain, is advantageous for a number of reasons. For example, a fluted wound drain has an increased tissue contact drainage area, increased luminal flow drainage area, and an increased cross-sectional area as compared to a perforated drain, resulting in increased fluidic throughput and increased strength. Moreover, the fluted configuration reduces the risk that tissue growth will inhibit removal of the drain.

The fluted wound drains disclosed in the Blake patents have been modified so as to enhance their suitability for certain purposes. For example, U.S. Pat. No. 6,976,973 to Ruddell et al. discloses a dual-lumen catheter for peritoneal dialysis that includes an "inflow" lumen allowing fluid to flow from outside the patient, through the catheter, and into the patient, and an "outflow" lumen allowing fluid to flow from the peritoneal cavity, through the catheter, and out of the patient. The outflow lumen may include a plurality of perforations, or alternatively a plurality of elongated slots through which fluid may flow out of the patient's body and a plurality of septa that partition the lumen. One such outflow lumen disclosed by Ruddell includes four slots and four septa, and appears generally similar to the fluted wound drain illustrated in FIGS. 1A-1E. FIG. 1F, which has been adapted from Ruddell, illustrates an alternative outflow lumen 88, which includes slots 80 on one side of a tube, a plurality of septa 82 defining lumens 86, an enclosed lumen 90 that may be part of the outflow lumen or party of the inflow lumen, and a radiopaque stripe 54. Ruddell discloses that slots 80 alternatively may be opposite from the radiopaque stripe (not shown here).

Although the fluted wound drains disclosed in the Blake patents and the peritoneal dialysis catheters disclosed by Ruddell may be partially implanted into a patient, both designs may have shortcomings rendering them unsuitable for long-term use, particularly within the peritoneal cavity. For example, slits 135 illustrated in FIG. 1B are equally susceptible to blockage as one another, as are slits 80 illustrated in FIG. 1F. In particular, if a wound drain or catheter having such slits is implanted in the peritoneum and a given portion of the patient's intestine drapes over the catheter, fluid flow through multiple of the slits potentially may be blocked simultaneously. Additionally, the catheter potentially may become ensnared in the greater omentum or the lesser omentum, which again may potentially block fluid flow through multiple of the slits simultaneously.

Accordingly, what is needed is a fluid drainage catheter with enhanced resistance to blockage.

SUMMARY OF INVENTION

Embodiments of the present invention provide implantable catheters with staggered slits, and methods of using the same. The inventive catheters include an elongate member having a plurality of slits defined therethrough, which allow fluid to pass into, or out of, lumen(s) within the elongate member. At least some of the slits have different lengths than one another, which enhances the likelihood that the lumen(s) may be blocked by debris or objects within the body.

Under one aspect of the present invention, a catheter includes an elongate member; a plurality of septa configured to define a plurality of lumens along the elongate member; and a plurality of slits defined through the elongate member, each slit configured to provide fluidic communication between an environment about the catheter and a corresponding lumen of the plurality of lumens, at least one slit having a different length than at least one other slit.

In some embodiments, the plurality of septa includes four septa configured to define four lumens along the elongate member. The plurality of slits may include four slits. Each slit of the four slits may have a different length than each other slit of the four slits. Alternatively, two slits of the four slits may have the same length as one another. The other two slits of the four slits also may have the same length as one another, but the length is different than the length of the previously mentioned two slits.

In some embodiments, the septa extend for less than the entire length of the elongate member. A proximal end of the elongate member may have only a single lumen defined therethrough.

In some embodiments, the elongate member has a proximal end and a distal end, the proximal end configured to be coupled to an external device, the distal end configured to be implanted within a patient's body. In other embodiments, the proximal end is configured to be coupled to an implantable device, and the distal end is configured to be implanted within a patient's body.

Under another aspect of the present invention, a method of using a catheter includes: providing a catheter including an elongate member having a proximal end and a distal end; a plurality of septa configured to define a plurality of lumens along the elongate member; and a plurality of slits defined through the elongate member, each slit configured to provide fluidic communication between an environment about the catheter and a corresponding lumen of the plurality of lumens, at least one slit having a different length than at least one other slit; and implanting the distal end of the elongate member within a patient.

BRIEF DESCRIPTION OF DRAWINGS

FIGS. 1A-1F illustrate various views of prior art fluid drainage catheters.

FIG. 2A is a perspective view of a catheter with staggered slits according to some embodiments of the present invention, in which the broken line in the region that is designated "FIG. 6A" indicates a slit that is on the underside of the catheter.

DETAILED DESCRIPTION

Figure 2B:
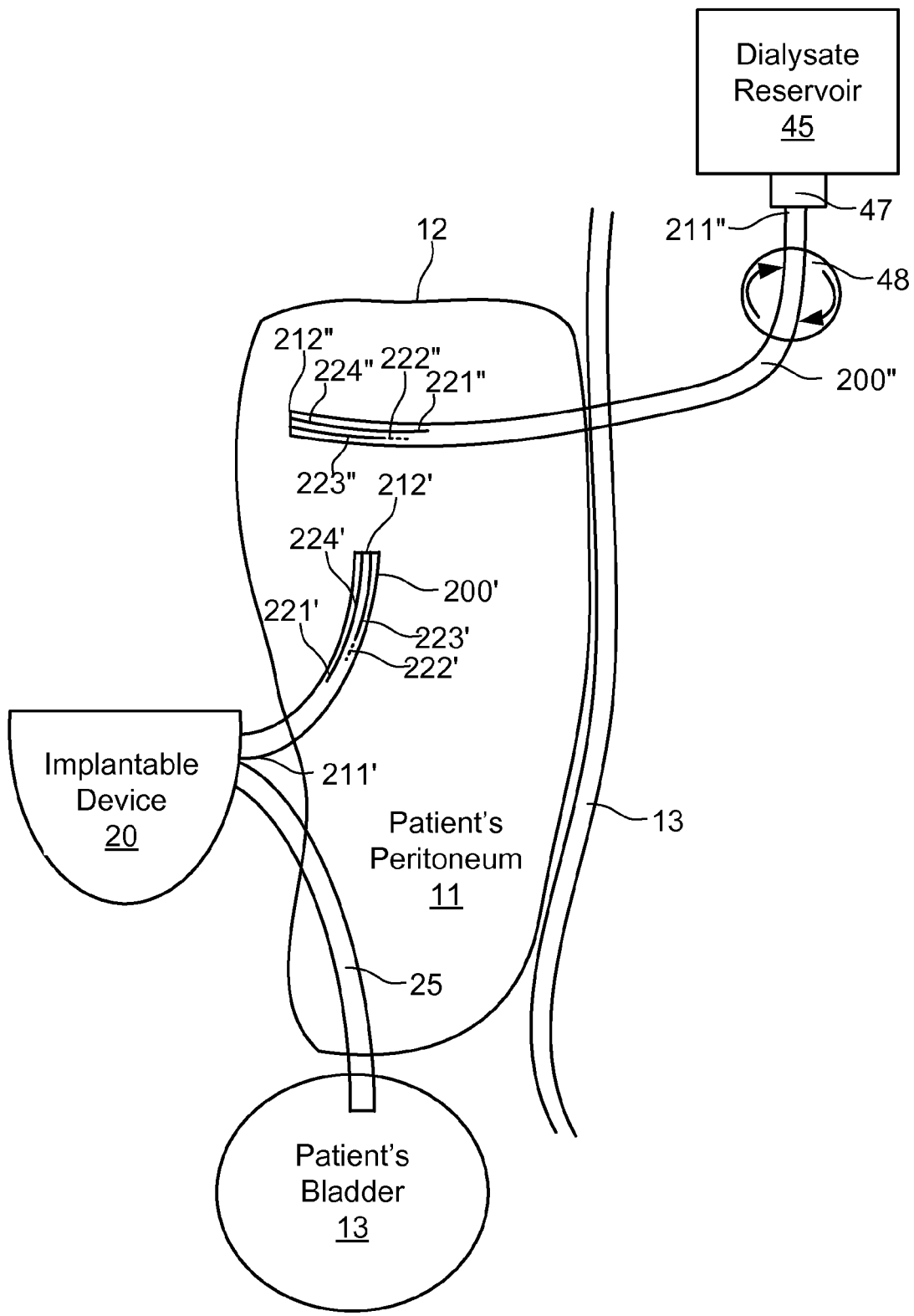
FIG. 2B illustrates the catheter of FIG. 2A as implanted in a patient for use in peritoneal dialysis.

Embodiments of the present invention provide implantable catheters with staggered slits, and methods of using the same. Such catheters are fully implantable with the body, and are provide enhanced resistance to blockage. Specifically, the catheters include a generally tubular elongate member, in which a plurality of slits are defined. In contrast to the slits disclosed in the Blake patents and in Ruddell, the inventive slits are of different lengths than one another; that is, the slits are "staggered" along the length of the elongate member. As such, the slits provide fluidic communication between an environment, e.g., a patient's peritoneal cavity, and lumen(s) within the elongate member, but have a reduced susceptibility to blockage because any potential source of blockage, such as a portion of the patient's intestine, lesser omentum, or greater omentum, is unlikely to simultaneously block all of the slits at once due to their staggered configuration. The staggered slits thus render the catheters suitable to be fully implanted for environments having many potential sources of blockage, for relatively long periods of time. The inventive catheters may be used both to withdraw fluid from an environment, and to distribute fluid to an environment, as desired.

FIG. 2A illustrates a perspective view of an implantable fluid drainage catheter 200 according to some embodiments of the present invention. Catheter 200 includes continuous elongate member 210 having proximal end 211 and distal end 212. Elongate member 210 may be formed of any suitable flexible, biocompatible material such as medical-grade silicone, and optionally which may include radiopaque stripe 240 formed of a suitable material that imparts radiopacity to elongate member 210 when fluoroscopically imaged. As described in greater detail below with reference to FIGS. 4A-9B, catheter 200 also includes an internal core portion that extends along a portion of the length of elongate member 210, and that includes septa that define a plurality of lumens 232 that extend along the same portion of the length of the elongate member as does the core portion. A plurality of slits 221, 222, 223, and 224 are defined in elongate member 210 so as to provide fluidic access between an environment, e.g., a patient's peritoneal cavity, and lumens 232. Note that in FIG. 2A, slit 224 is obscured by slit 221.

In the embodiment illustrated in FIG. 2A, slits 221, 222, 223, and 224 are all of different length than one another, and are staggered along the length of elongate member 210, so as to provide catheter 200 with reduced susceptibility to blockage. Specifically, elongate member 210 has a length L1, along which the cross-section and external surface of the elongate member varies as described further below with reference to FIGS. 3A-9A. In the region of FIG. 2A generally designated "FIG. 3A," a portion of elongate member 210 having length L2 is hollow, has a single lumen defined therethrough, and includes proximal end 211, as described in greater detail below with reference to FIGS. 3A-3B. In the region of FIG. 2A generally designated "FIG. 4A," a portion of elongate member 210 having length L3 includes a core portion and four septa that extend collinearly with elongate member 210, and that define four collinear lumens therethrough, as described in greater detail below with reference to FIGS. 4A-4B. In the region of FIG. 2A generally designated "FIG. 5A," a portion of elongate member 210 having length L4 includes the core portion and four septa, as well as first slit 221 defined in elongate member 210, as described in greater detail below with reference to FIGS. 5A-5B. In the region of FIG. 2A generally designated "FIG. 6A," a portion of elongate member 210 having length L4 includes the core portion, four septa, first slit 221, and second slit 222 defined in elongate member 210, as described in greater detail below with reference to FIGS. 6A-6B. Note that second slit 222 is illustrated using a broken line to indicate that the slit is on the underside of the catheter. In the region of FIG. 2A generally designated "FIG. 7A," a portion of elongate member 210 having length L4 includes the core portion, four septa, first slit 221, second slit 222, and third slit 223 defined in elongate member 210, as described in greater detail below with reference to FIGS. 7A-7B. In the region of FIG. 2A generally designated "FIG. 8A," a portion of elongate member 210 having length L4 includes the core portion, four septa, first slit 221, second slit 222, third slit 223, and fourth slit 224 defined in elongate member 210, as described in greater detail below with reference to FIGS. 8A-8B. Note that fourth slit 224 is obscured by first slit 221 in FIG. 2A, but may be seen in FIGS. 8A-8B. In the region of FIG. 2A generally designated "FIG. 9A," a portion of elongate member 210 having length L5 includes the core portion, four septa, first slit 221, second slit 222, third slit 223, and fourth slit 224 and includes distal end 212, as described in greater detail below with reference to FIGS. 9A-9B.

In some embodiments, length L1 of elongate member 210 is selected so as to render elongate member 210 compatible with the environment in which it is to be used. Lengths between about 100 mm and about 1000 mm may be suitable for many applications. For example, for embodiments in which elongate member 210 is to be implanted within an adult patient's peritoneum, elongate member 210 may have a length L1 between about 250 mm and about 750 mm, e.g., between about 300 mm and about 600 mm, or between about 300 mm and about 500 mm, or, in one exemplary embodiment, about 400 mm. Lengths L2, L3, L4, and L5 suitably may be selected such that slits 221, 222, 223, 224 are sufficiently long as to permit sufficient fluid withdrawal from, or sufficient fluid distribution to, an environment. For example, in one exemplary embodiment, length L2 is approximately 100 mm, length L3 is approximately 50 mm, length L4 is approximately 25 mm, and length L5 is approximately 175 mm. It should be appreciated that other lengths L1, L2, L3, L4, and L5 suitably may be used. Furthermore, the slits need not be staggered by the same length as one another, that is, each length L4 illustrated in FIG. 2A may be different from one another, although in some embodiments these lengths L4 are the same as one another.

FIG. 2B illustrates a plan view of catheter 200 as configured in two different manners for use in peritoneal dialysis. Specifically, first catheter 200' is fully implanted within a patient's body, with the majority of catheter 200' being within the patient's peritoneum 11, which is bounded by peritoneal membrane 12. Proximal end 211' of first catheter 200' may be coupled to implantable device 20, while distal end 212' of first catheter 200' may be disposed in peritoneum 11. First catheter 200' includes staggered slits 221', 222', 223', and 224' that are configured to provide fluidic communication between peritoneum 11 and implantable device 20 through lumen(s) inside catheter 200', allowing the implantable device to withdraw fluid from peritoneum 11 through catheter 200' with reduced likelihood of blockage. Specifically, as described in greater detail in U.S. patent application Ser. No. 13/397,498, filed Feb. 15, 2102 and entitled "Systems and Methods for Treating Chronic Liver Failure Based on Peritoneal Dialysis," the entire contents of which are incorporated by reference herein, implantable device 20 may include an electromechanical pump that is configured for subcutaneous implantation, an inlet port coupled to first catheter 200' (noting that the U.S. Ser. No. 13/397,498 discloses a catheter having apertures rather than staggered slits), and an outlet port coupled to bladder catheter 25. Bladder catheter 25 includes a tube having a first (proximal) end configured to be coupled to the pump outlet and a second (distal) end configured to be inserted through the wall of, and fixed within, a patient's bladder. When actuated, implantable device 20 withdraws fluid from peritoneum 11 through catheter 200' and pumps that fluid into bladder 13 through bladder catheter 25'; the patient then may excrete the fluid.

Second catheter 200" is partially implanted within peritoneum 11, with its proximal end 211" coupled to external dialysate reservoir 45 and its distal end 212" disposed in peritoneum 11. Second catheter 200" includes staggered slits 221", 222", 223", and 224" that are configured to provide fluidic communication between peritoneum 11 and dialysate reservoir 45 through lumen(s) inside catheter 200", allowing the dialysate reservoir 45 to deliver fluid to peritoneum 11 through catheter 200" with reduced likelihood of blockage. Specifically, reservoir 45 is configured to deliver albumin-containing peritoneal dialysis fluid (also referred to herein as dialysate, peritoneal dialysate, or fluid) to the patient's peritoneal cavity via second catheter 200". Proximal end 211" of second catheter 200" may be configured to be removably coupled to external dialysate reservoir 45 via an appropriate coupling 47, allowing the patient to easily exchange a depleted reservoir for a fresh one. Distal end 212" of second catheter 200" may configured for implantation in the patient's peritoneum 11, with a tissue cuff (not shown) to promote tissue ingrowth at the point at which catheter 200" crosses the patient's skin 13. Reservoir 45 may deliver the peritoneal dialysis fluid to the peritoneal cavity by any suitable mechanism. For example, an external pump 48 may be used to facilitate fluid flow from the reservoir 45 to the peritoneum, or the reservoir may be physically raised above the level of the peritoneum such that gravity draws the peritoneal dialysis fluid into the peritoneum via catheter 200".

In other embodiments disclosed in U.S. Ser. No. 13/397, 498, the distal end of catheter 200" instead may be attached to the inlet port of implantable device 20, and implantable device 20 may be configured to pump the peritoneal dialysis fluid from reservoir 45 into the peritoneal cavity via a standard (non-slitted) catheter and first catheter 200'. In such embodiments, reservoir 45 may be external or implantable, and implantable device 45 further may include one or more passive or active valves to prevent fluid from being pumped out of the bladder and into the peritoneum at the same time that fluid is pumped from the reservoir and into the peritoneum.

In a preferred embodiment, first catheter 200' and second catheter 200" both are made of medical-grade silicone and include polyester cuffs at their distal ends (not shown) to maintain the catheters in position. Additionally, it should be understood that catheters 200' and 200" need not necessarily be used in conjunction with one another, not need they necessarily be used for peritoneal dialysis. For example, second catheter 200" and dialysate reservoir 45 may be omitted, and first catheter 200' and implantable device 20 instead may be used with withdraw ascites from peritoneum 11 and pump the ascites into bladder 13 for excretion. Indeed, the inventive catheters may be partially or fully implanted as desired, may be coupled to any suitable implanted or external device via an appropriate coupling, and may be used to withdraw fluid from, or distribute fluid to, any suitable portion(s) of a patient's body.

Additional detail of the structure of catheter 200 illustrated in FIG. 2A now will be provided. Further below, an alternative embodiment will be described.

Figure 3A:
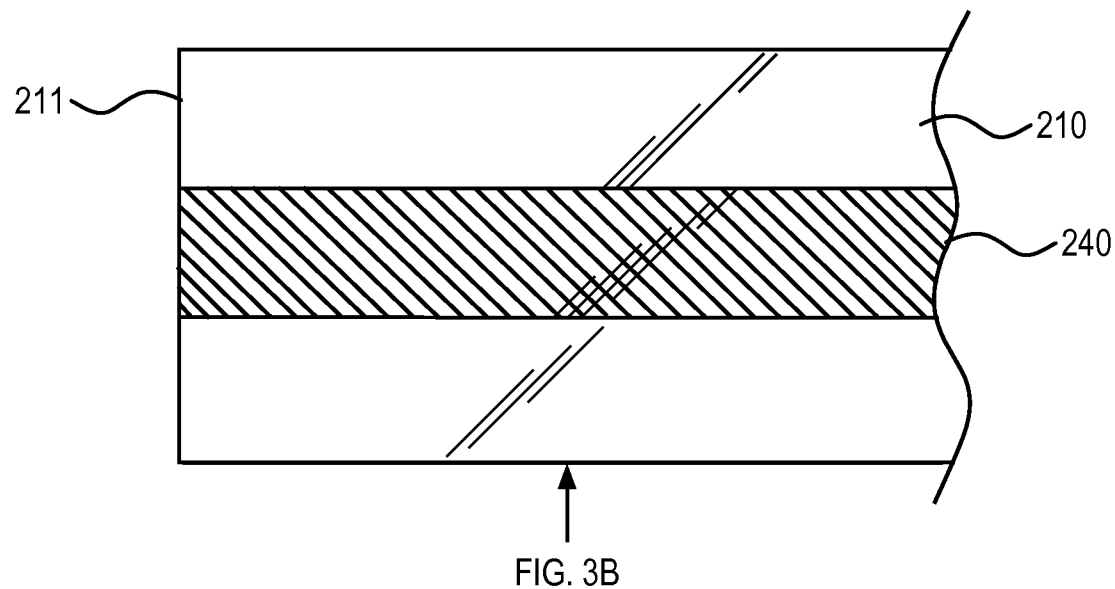
FIG. 3A is a perspective view of the catheter showing additional detail in the region of FIG. 2 that is designated "FIG. 3A."
Figure 3B:
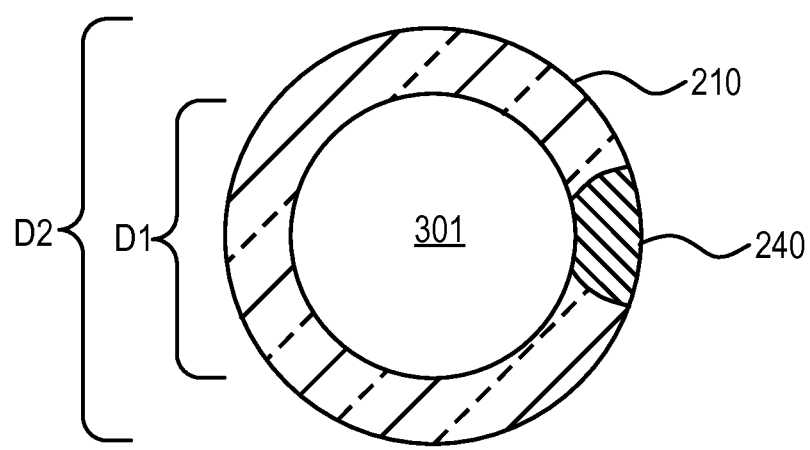
FIG. 3B is a cross-sectional view of the catheter in the region of FIG. 3A that is designated "FIG. 3B."

FIG. 3A is a perspective view of catheter 200 showing additional detail in the region of FIG. 2 that is designated "FIG. 3A," and FIG. 3B is a cross-sectional view of catheter 200 in the region of FIG. 3A that is designated "FIG. 3B." In this region, which includes proximal end 211, it may be seen that elongate member 210 is generally tubular and hollow, having a single lumen 301 defined therethrough. Proximal end 211 may include an appropriate coupling (not shown) to facilitate coupling between catheter 200 and another structure, e.g., an implantable or external device.

As illustrated in FIG. 3B, elongate member 210 has an inner diameter D1 and an outer diameter D2, which diameters are substantially uniform along the length of elongate member 210 and may be suitably selected to be compatible with the intended use of catheter 200. For example, inner diameter D1 suitably may vary between about 1 mm and about 10 mm, and outer diameter suitably may vary between about 2 mm and about 11 mm as appropriate, based on inner diameter D1. In some embodiments, D1 may be between about 1 mm and 4 mm, or between about 2 mm and 3 mm, in one illustrative embodiment about 2.7 mm. In some embodiments, D2 may be between about 2 mm and about 8 mm, or between about 3 mm and about 7 mm, or between about 4 mm and about 6 mm, in one illustrative embodiment about 5.1 mm.

Figure 4A:
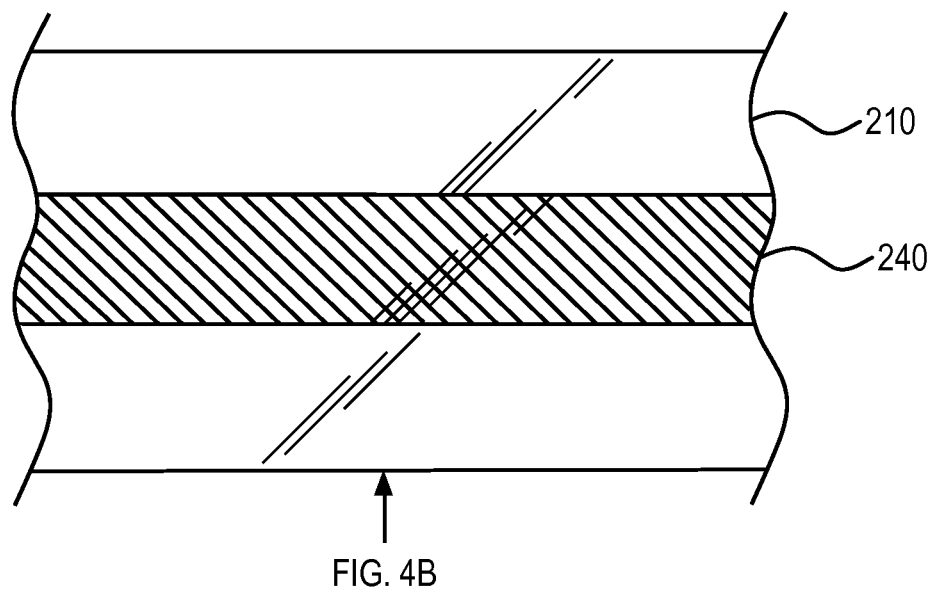
FIG. 4A is a perspective view of the catheter showing additional detail in the region of FIG. 2 that is designated "FIG. 4A."
Figure 4B:
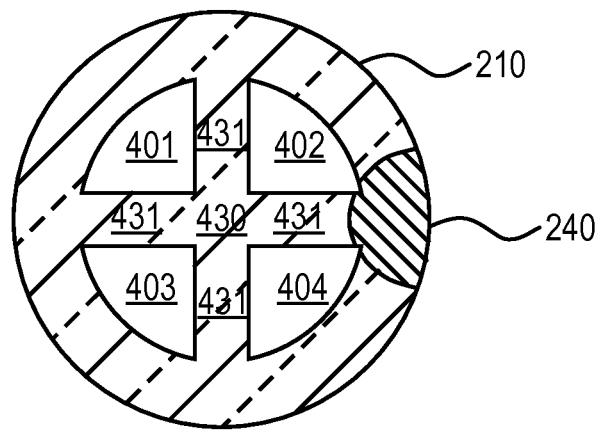
FIG. 4B is a cross-sectional view of the catheter in the region of FIG. 4A that is designated "FIG. 4B."

FIG. 4A is a perspective view of catheter 200 showing additional detail in the region of FIG. 2 that is designated "FIG. 4A," and FIG. 4B is a cross-sectional view of catheter 200 in the region of FIG. 4A that is designated "FIG. 4B." In this region, it may be seen that elongate member 210 includes core portion 430 and four septa 431 that define first, second, third, and fourth lumens 401, 402, 403, 404 that extend collinearly through elongate member 210. Note that elongate member 210, core portion 430, and septa 431 may be of unitary construction with one another, e.g., made of the same material as one another in a common process. For example, elongate member 210, core portion 430, and septa 431 may be co-extruded through a suitable die. It will be appreciated that catheters produced using such a manufacturing process may have corners and angles that are not necessarily as sharp or as well-defined as illustrated in the figures.

Figure 5A:
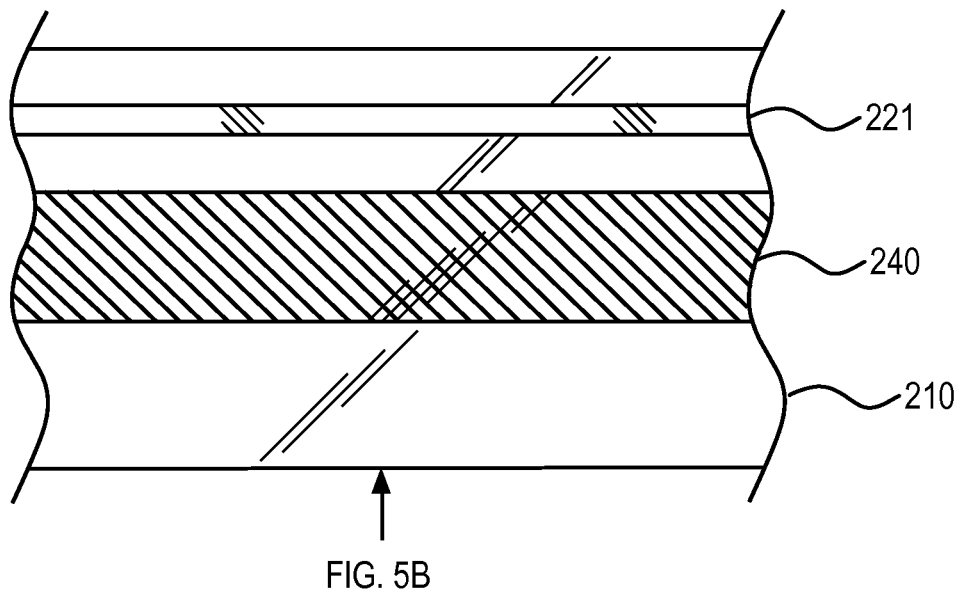
FIG. 5A is a perspective view of the catheter showing additional detail in the region of FIG. 2 that is designated "FIG. 5A."
Figure 5B:
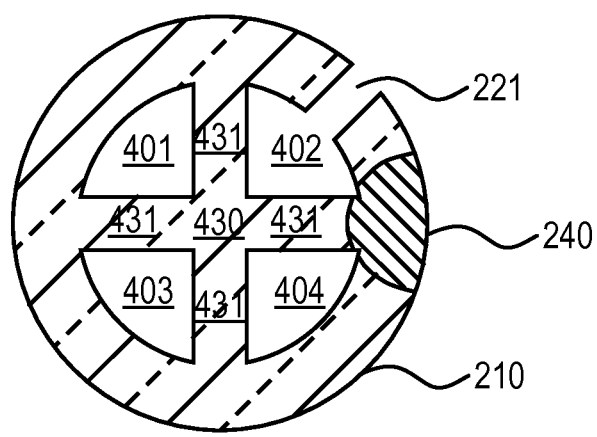
FIG. 5B is a cross-sectional view of the catheter in the region of FIG. 5A that is designated "FIG. 5B."

FIG. 5A is a perspective view of catheter 200 showing additional detail in the region of FIG. 2 that is designated "FIG. 5A," and FIG. 5B is a cross-sectional view of catheter 200 in the region of FIG. 5A that is designated "FIG. 5B." In this region, it may be seen that elongate member 210 includes core portion 430 and four septa 431, which may be continuations of core portion 430 and septa 431 illustrated in FIG. 4B, and that define first, second, third, and fourth lumens 401, 402, 403, 404 that extend collinearly through elongate member 210 and may be continuations of lumens 401, 402, 403, 404 illustrated in FIG. 4B. In this region, first slit 221 is defined through elongate member 210 so as to provide fluidic communication between an environment and lumen 402.

Figure 6A:
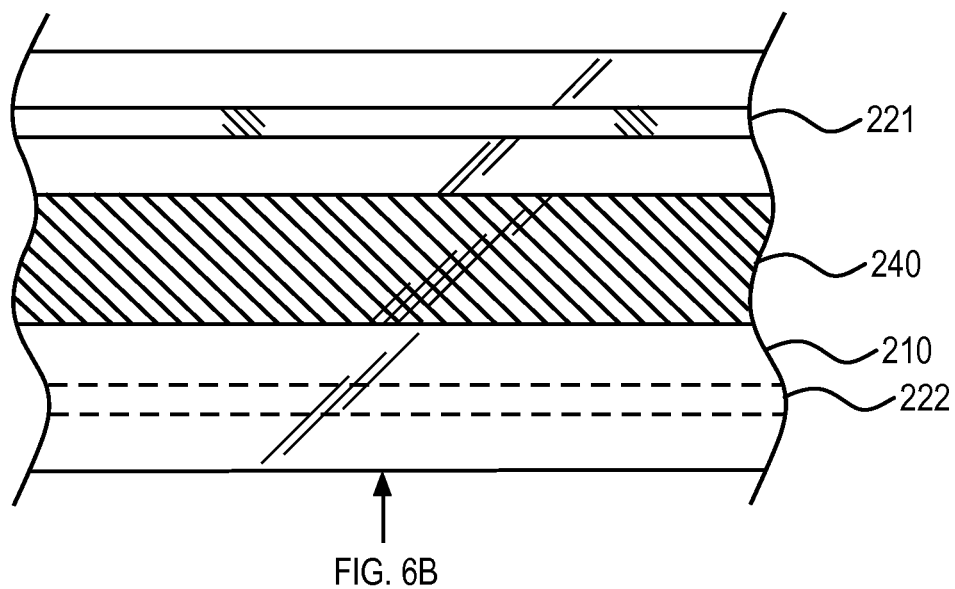
FIG. 6A is a perspective view of the catheter showing additional detail in the region of FIG. 2 that is designated "FIG. 6A," and in which the dashed lines indicate a slit that is on the underside of the catheter.
Figure 6B:
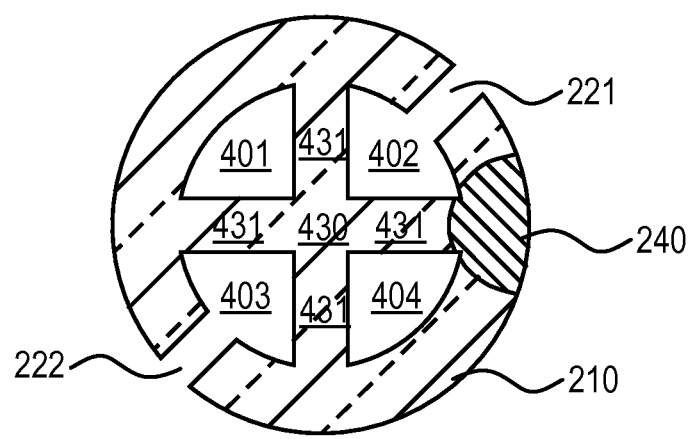
FIG. 6B is a cross-sectional view of the catheter in the region of FIG. 6A that is designated "FIG. 6B."

FIG. 6A is a perspective view of catheter 200 showing additional detail in the region of FIG. 2 that is designated "FIG. 6A," and FIG. 6B is a cross-sectional view of catheter 200 in the region of FIG. 6A that is designated "FIG. 6B." In this region, it may be seen that elongate member 210 includes core portion 430 and four septa 431, which may be continuations of core portion 430 and septa 431 illustrated in FIGS. 4B-5B, and that define first, second, third, and fourth lumens 401, 402, 403, 404 that extend collinearly through elongate member 210 and may be continuations of lumens 401, 402, 403, 404 illustrated in FIGS. 4B-5B. In this region, first slit 221 is defined through elongate member 210 so as to provide fluidic communication between the environment and lumen 402, and second slit 222 is defined through elongate member 210 so as to provide fluidic communication between the environment and lumen 403. Note that second slit 222 is illustrated with broken lines to indicate that the slit is on the underside of catheter 200.

Figure 7A:
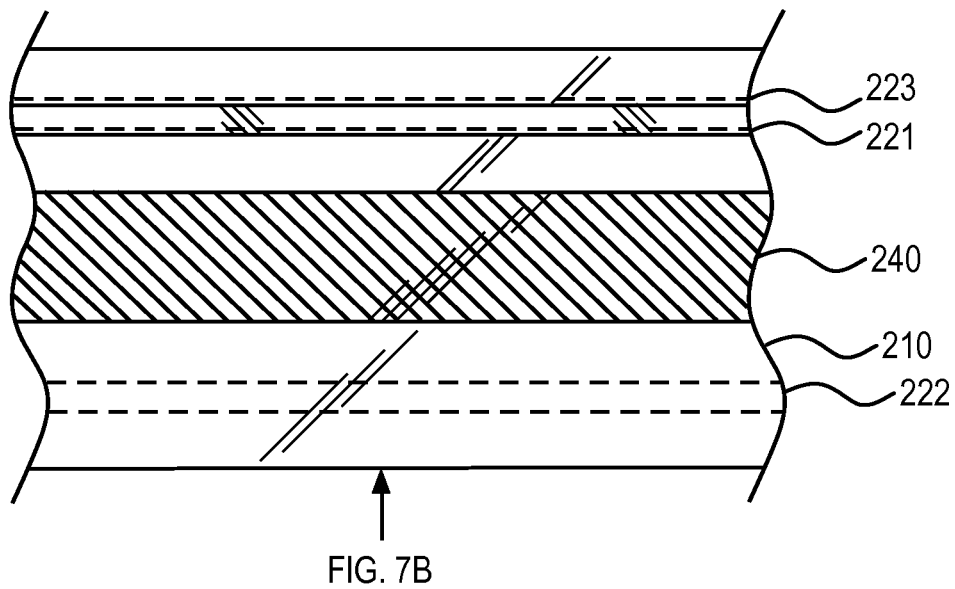
FIG. 7A is a perspective view of the catheter showing additional detail in the region of FIG. 2 that is designated "FIG. 7A," and in which the dashed lines indicate slits that are on the underside of the catheter.
Figure 7B:
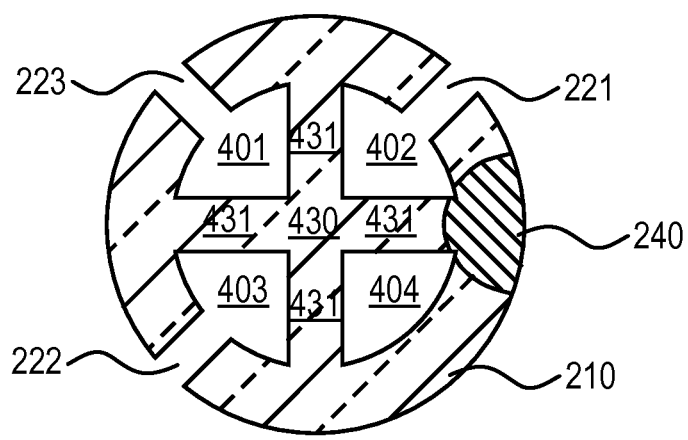
FIG. 7B is a cross-sectional view of the catheter in the region of FIG. 7A that is designated "FIG. 7B."

FIG. 7A is a perspective view of catheter 200 showing additional detail in the region of FIG. 2 that is designated "FIG. 7A," and FIG. 7B is a cross-sectional view of catheter 200 in the region of FIG. 7A that is designated "FIG. 7B." In this region, it may be seen that elongate member 210 includes core portion 430 and four septa 431, which may be continuations of core portion 430 and septa 431 illustrated in FIGS. 4B-6B, and that define first, second, third, and fourth lumens 401, 402, 403, 404 that extend collinearly through elongate member 210 and may be continuations of lumens 401, 402, 403, 404 illustrated in FIGS. 4B-6B. In this region, first slit 221 is defined through elongate member 210 so as to provide fluidic communication between the environment and lumen 402, second slit 222 is defined through elongate member 210 so as to provide fluidic communication between the environment and lumen 403, and third slit 223 is defined through elongate member 210 so as to provide fluidic communication between the environment and lumen 401.

Figure 8A:
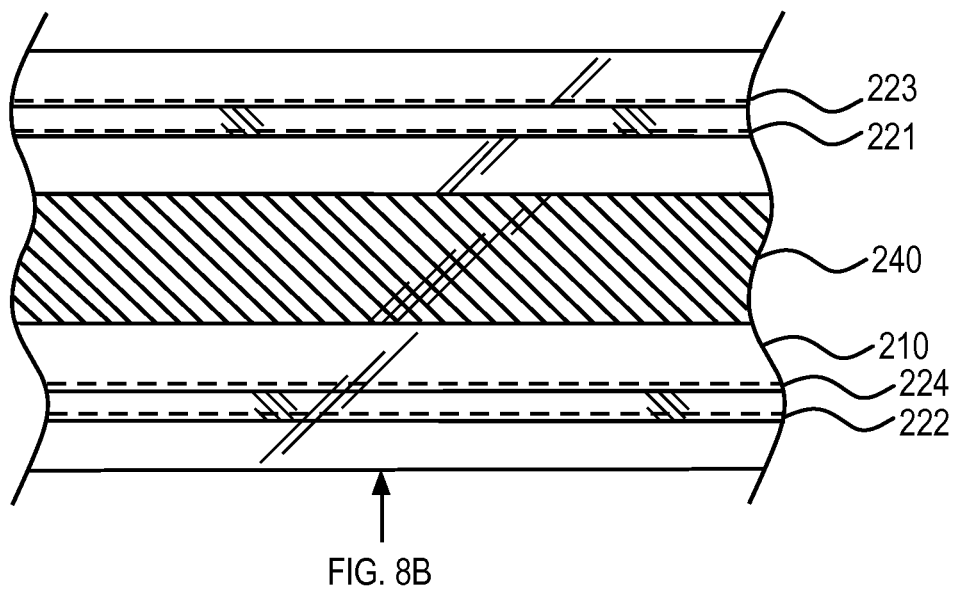
FIG. 8A is a perspective view of the catheter showing additional detail in the region of FIG. 2 that is designated "FIG. 8A," and in which the dashed lines indicate slits that are on the underside of the catheter.
Figure 8B:
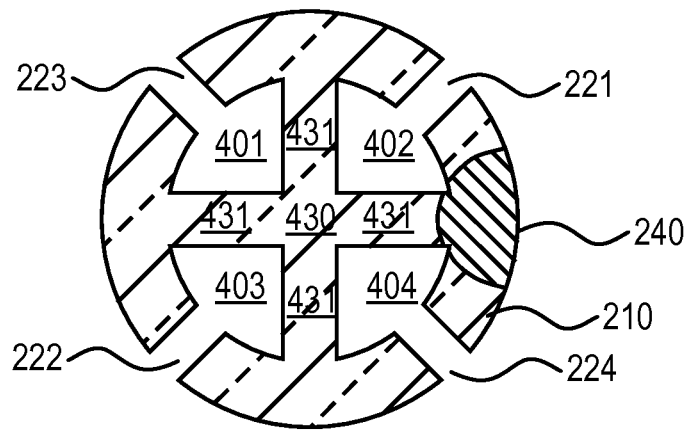
FIG. 8B is a cross-sectional view of the catheter in the region of FIG. 8A that is designated "FIG. 8B."

FIG. 8A is a perspective view of catheter 200 showing additional detail in the region of FIG. 2 that is designated "FIG. 8A," and FIG. 8B is a cross-sectional view of catheter 200 in the region of FIG. 8A that is designated "FIG. 8B." In this region, it may be seen that elongate member 210 includes core portion 430 and four septa 431, which may be continuations of core portion 430 and septa 431 illustrated in FIGS. 4B-7B, and that define first, second, third, and fourth lumens 401, 402, 403, 404 that extend collinearly through elongate member 210 and may be continuations of lumens 401, 402, 403, 404 illustrated in FIGS. 4B-7B. In this region, first slit 221 is defined through elongate member 210 so as to provide fluidic communication between the environment and lumen 402, second slit 222 is defined through elongate member 210 so as to provide fluidic communication between the environment and lumen 403, third slit 223 is defined through elongate member 210 so as to provide fluidic communication between the environment and lumen 401, and fourth slit 224 is defined through elongate member 210 so as to provide fluidic communication between the environment and lumen 404. Note that fourth slit 224 is illustrated with broken lines to indicate that the slit is on the underside of catheter 200.

Figure 9A:
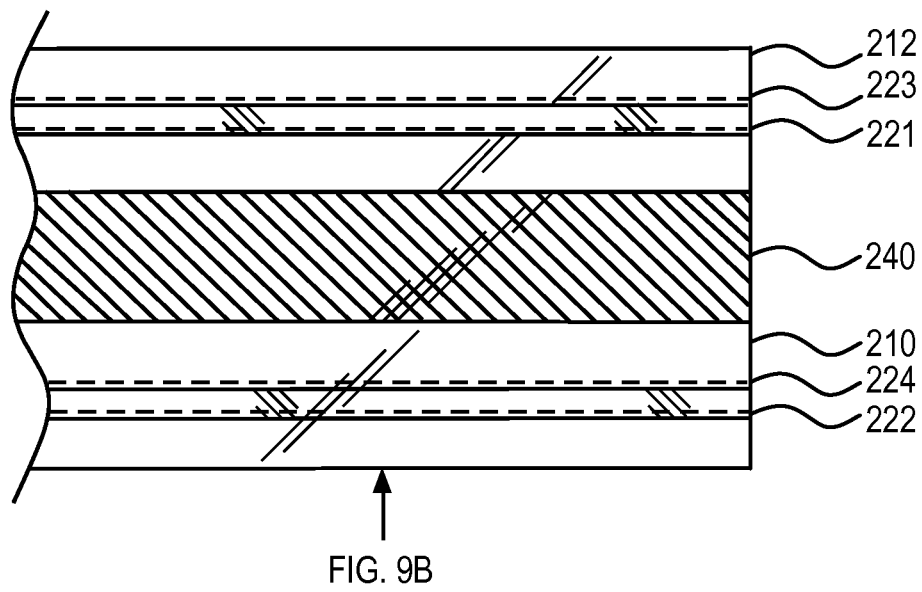
FIG. 9A is a perspective view of the catheter showing additional detail in the region of FIG. 2 that is designated "FIG. 9A," and in which the dashed lines indicate slits that are on the underside of the catheter.
Figure 9B:
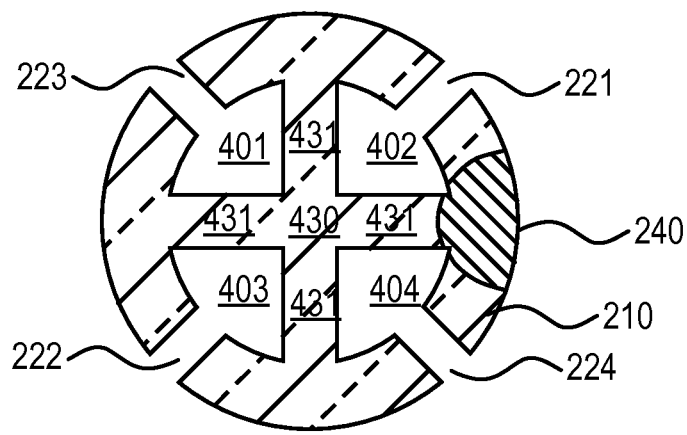
FIG. 9B is a cross-sectional view of the catheter in the region of FIG. 9A that is designated "FIG. 9B."

FIG. 9A is a perspective view of catheter 200 showing additional detail in the region of FIG. 2 that is designated "FIG. 9A," and FIG. 9B is a cross-sectional view of catheter 200 in the region of FIG. 9A that is designated "FIG. 9B." In this region, which includes distal end 212 of catheter 200, it may be seen that elongate member 210 includes core portion 430 and four septa 431, which may be continuations of core portion 430 and septa 431 illustrated in FIGS. 4B-8B, and that define first, second, third, and fourth lumens 401, 402, 403, 404 that extend collinearly through elongate member 210 and may be continuations of lumens 401, 402, 403, 404 illustrated in FIGS. 4B-8B. In this region, first slit 221 is defined through elongate member 210 so as to provide fluidic communication between the environment and lumen 402, second slit 222 is defined through elongate member 210 so as to provide fluidic communication between the environment and lumen 403, third slit 223 is defined through elongate member 210 so as to provide fluidic communication between the environment and lumen 401, and fourth slit 224 is defined through elongate member 210 so as to provide fluidic communication between the environment and lumen 404.

An alternative embodiment of a catheter with staggered slits now will be described with reference to FIGS. 10-15B.

Figure 10:
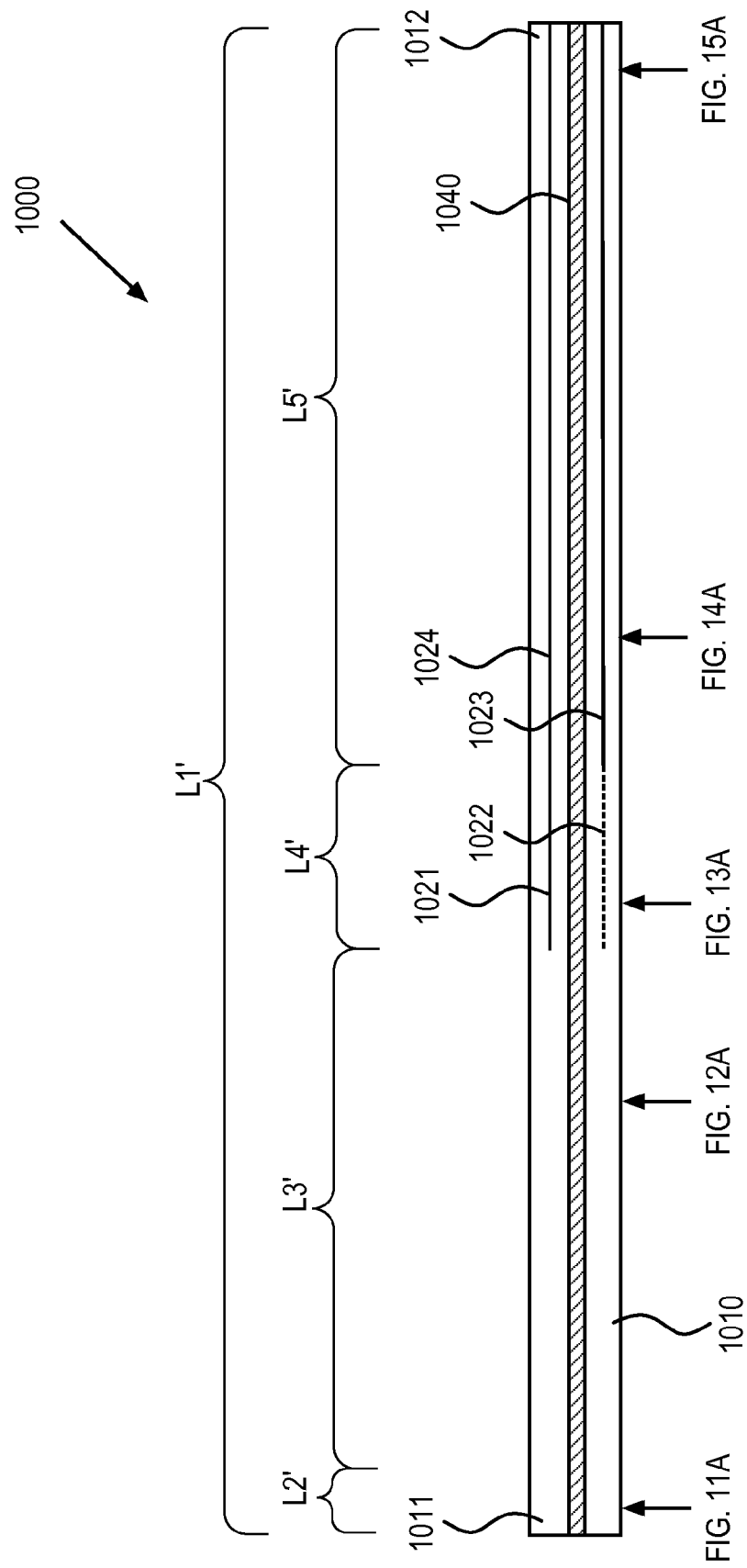
FIG. 10 is a perspective view of an alternative catheter with staggered slits according to some embodiments of the present invention, in which the broken line in the region that is designated "FIG. 4A" indicates a slit that is on the underside of the catheter.

FIG. 10 illustrates a perspective view of an implantable fluid drainage catheter 1000 according to an alternative embodiment of the present invention. Catheter 1000 includes continuous elongate member 1010 having proximal end 1011 and distal end 1012. Elongate member 1010 may be formed of any suitable flexible, biocompatible material such as medical-grade silicone, and optionally which may include radiopaque stripe 1040 formed of a suitable material that imparts radiopacity to elongate member 1010 when fluoroscopically imaged. As described in greater detail below with reference to FIGS. 11A-15B, catheter 1000 also includes an internal core portion that extends along a portion of the length of elongate member 1010, and that includes septa that define a plurality of lumens that extend along the same portion of the length of the elongate member as does the core portion. A plurality of slits 1021, 1022, 1023, and 1024 are defined in elongate member 1010 so as to provide fluidic access between an environment, e.g., a patient's peritoneal cavity, and the lumens of elongate member 1010. Note that in FIG. 10, slit 1024 is obscured by slit 1021.

In the embodiment illustrated in FIG. 10, slits 1021 and 1022 are the same length as one another, and slits 1023 and 1024 are the same length as one another but a different length than slits 1021 and 1022, so as to provide catheter 1000 with reduced susceptibility to blockage. Specifically, elongate member 1010 has a length L1', along which the cross-section and external surface of the elongate member varies as described further below with reference to FIGS. 11A-15B. In the region of FIG. 10 generally designated "FIG. 11A," a portion of elongate member 1010 having length L2' is hollow, has a single lumen defined therethrough, and includes proximal end 1011, as described in greater detail below with reference to FIGS. 11A-11B. In the region of FIG. 10 generally designated "FIG. 12A," a portion of elongate member 1010 having length L3' includes a core portion and four septa that extend collinearly with elongate member 1010, and that define four collinear lumens therethrough, as described in greater detail below with reference to FIGS. 12A-12B. In the region of FIG. 10 generally designated "FIG. 13A," a portion of elongate member 1010 having length L4' includes the core portion and four septa, as well as first and second slits 1021, 1022 defined in elongate member 1010, as described in greater detail below with reference to FIGS. 13A-13B. In the region of FIG. 10 generally designated "FIG. 14A," a portion of elongate member 1010 having length L5' includes the core portion, four septa, first slit 1021, and second slit 1022, third slit 1023, and fourth slit 1024 defined in elongate member 1010, as described in greater detail below with reference to FIGS. 14A-14B. Note that fourth slit 1024 is obscured by first slit 1021 in FIG. 10, but may be seen in FIGS. 14A-14B. In the region of FIG. 10 generally designated "FIG. 15A," a portion of elongate member 1010 having length L5' includes the core portion, four septa, first slit 1021, second slit 1022, third slit 1023, and fourth slit 1024 and includes distal end 1012, as described in greater detail below with reference to FIGS. 15A-15B.

In some embodiments, length L1' of elongate member 1010 is selected so as to render elongate member 1010 compatible with the environment in which it is to be used, and may be selected similarly as described above for length L1 of elongate member 210. Lengths L2', L3', L4', and L5' suitably may be selected such that slits 1021, 1022, 1023, 1024 are sufficiently long as to permit sufficient fluid withdrawal from, or sufficient fluid distribution to, an environment. For example, in one exemplary embodiment, length L2' is approximately 10 mm, length L3' is approximately 120 mm, length L4' is approximately 50 mm, and length L5' is approximately 220 mm. It should be appreciated that other lengths L1', L2', L3', L4', and L5' suitably may be used.

Figure 11A:
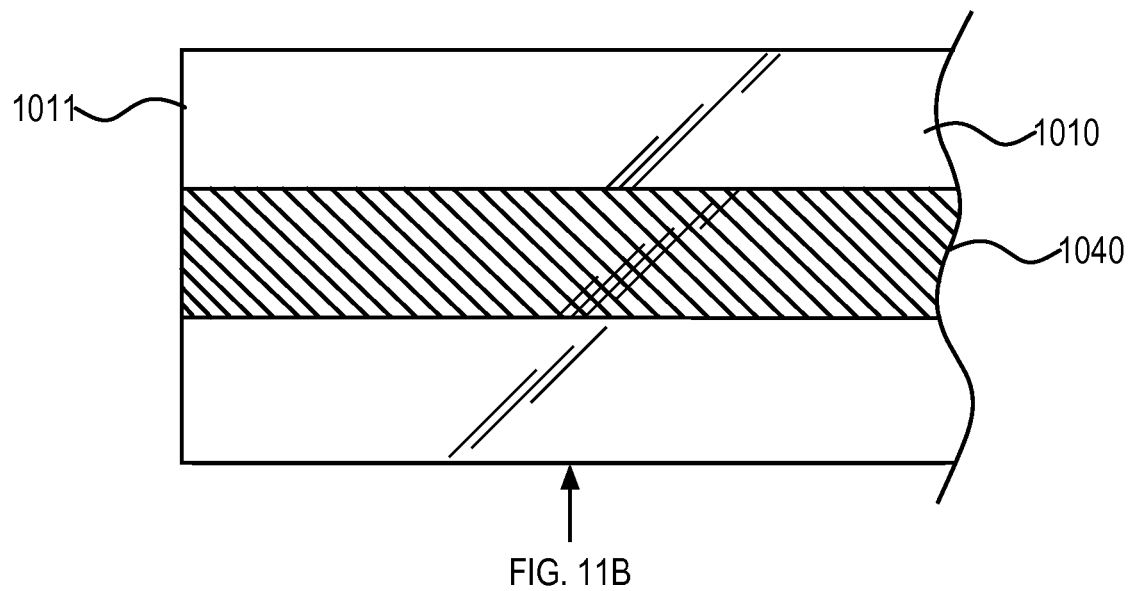
FIG. 11A is a perspective view of the catheter showing additional detail in the region of FIG. 10 that is designated "FIG. 11A."
Figure 11B:
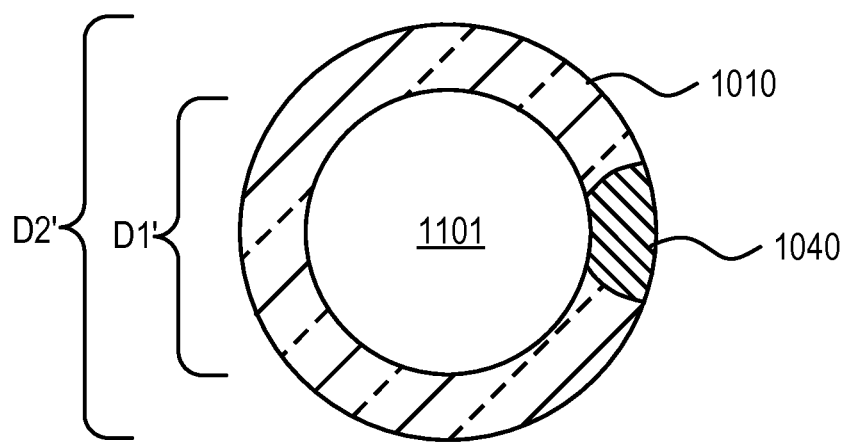
FIG. 11B is a cross-sectional view of the catheter in the region of FIG. 11A that is designated "FIG. 11B."

FIG. 11A is a perspective view of alternative catheter 1000 showing additional detail in the region of FIG. 10 that is designated "FIG. 11A," and FIG. 11B is a cross-sectional view of catheter 1000 in the region of FIG. 11A that is designated "FIG. 11B." In this region, which includes proximal end 1011, it may be seen that elongate member 1010 is generally tubular and hollow, having a single lumen 1101 defined therethrough. Proximal end 1011 may include an appropriate coupling (not shown) to facilitate coupling between catheter 1000 and another structure, e.g., an implantable or external device. As illustrated in FIG. 11B, elongate member 1010 has an inner diameter D1' and an outer diameter D2', which diameters are substantially uniform along the length of elongate member 1010 and may be suitably selected to be compatible with the intended use of catheter 1000, e.g., as described above for inner diameter D1 and outer diameter D2 of catheter 200.

Figure 12A:
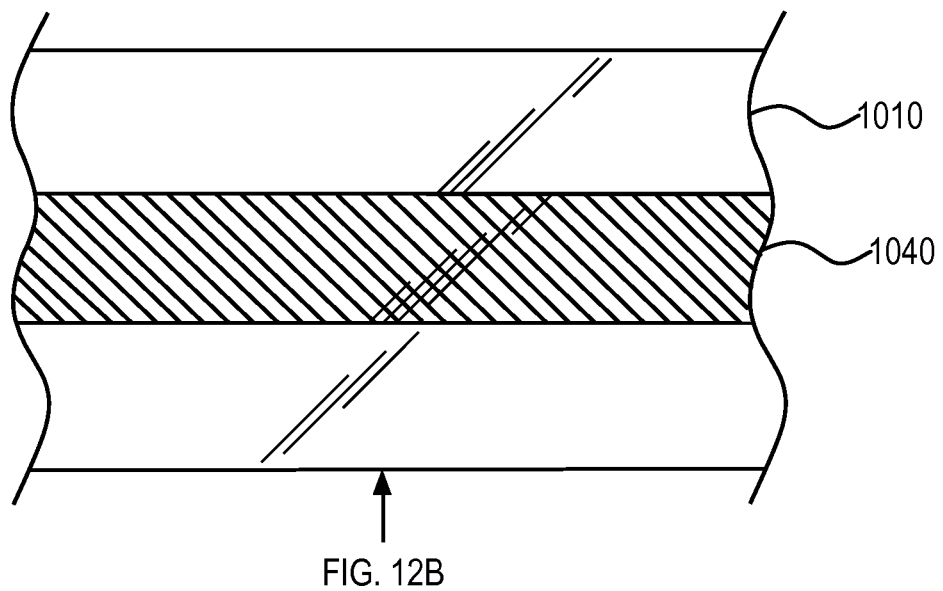
FIG. 12A is a perspective view of the catheter showing additional detail in the region of FIG. 10 that is designated "FIG. 12A."
Figure 12B:
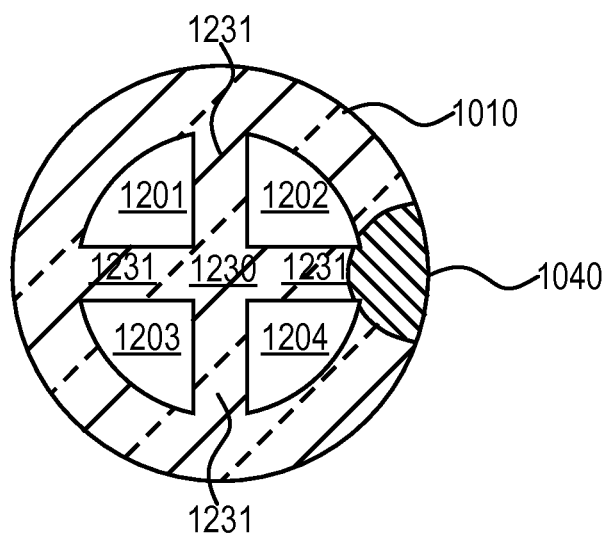
FIG. 12B is a cross-sectional view of the catheter in the region of FIG. 12A that is designated "FIG. 12B."

FIG. 12A is a perspective view of catheter 1000 showing additional detail in the region of FIG. 10 that is designated "FIG. 12A," and FIG. 12B is a cross-sectional view of catheter 1000 in the region of FIG. 12A that is designated "FIG. 12B." In this region, it may be seen that elongate member 1010 includes core portion 1230 and four septa 1231 that define first, second, third, and fourth lumens 1201, 1202, 1203, 1204 that extend collinearly through elongate member 1010. Note that elongate member 1010, core portion 1230, and septa 1231 may be of unitary construction with one another, e.g., made of the same material as one another. For example, elongate member 1010, core portion 1230, and septa 1231 may be co-extruded through a suitable die. It will be appreciated that catheters produced using such a manufacturing process may have corners and angles that are not necessarily as sharp or as well-defined as illustrated in the figures.

Figure 13A:
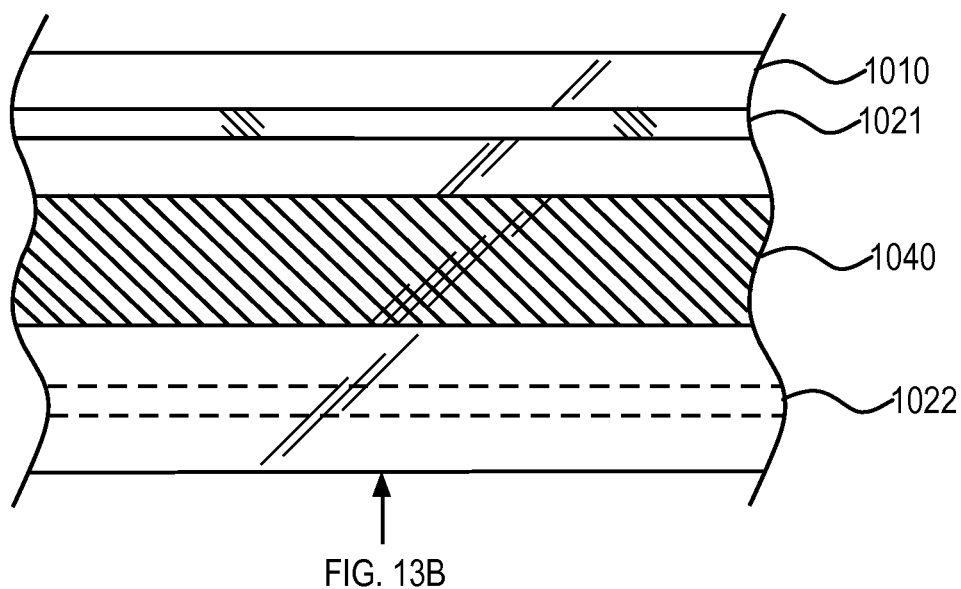
FIG. 13A is a perspective view of the catheter showing additional detail in the region of FIG. 10 that is designated "FIG. 13A," and in which the dashed lines indicate a slit that is on the underside of the catheter.
Figure 13B:
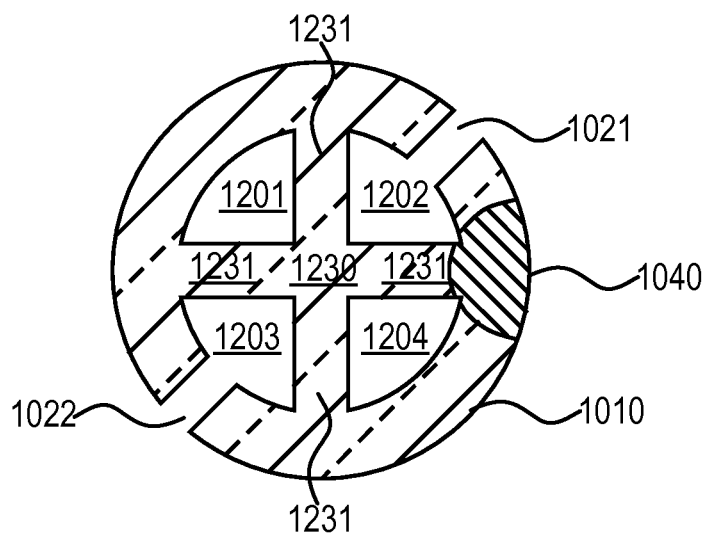
FIG. 13B is a cross-sectional view of the catheter in the region of FIG. 13A that is designated "FIG. 13B."

FIG. 13A is a perspective view of catheter 1000 showing additional detail in the region of FIG. 10 that is designated "FIG. 13A," and FIG. 13B is a cross-sectional view of catheter 1000 in the region of FIG. 13A that is designated "FIG. 13B." In this region, it may be seen that elongate member 1010 includes core portion 1230 and four septa 1231, which may be continuations of core portion 1230 and septa 1231 illustrated in FIG. 12B, and that define first, second, third, and fourth lumens 1201, 1202, 1203, 1204 that extend collinearly through elongate member 1010 and may be continuations of lumens 1201, 1202, 1203, 1204 illustrated in FIG. 12B. In this region, first slit 1021 and second slit 1022 are defined through elongate member 1010 so as to provide fluidic communication between an environment and lumens 1202, 1203, respectively. Note that second slit 1022 is illustrated with broken lines to indicate that the slit is on the underside of catheter 1000.

Figure 14A:
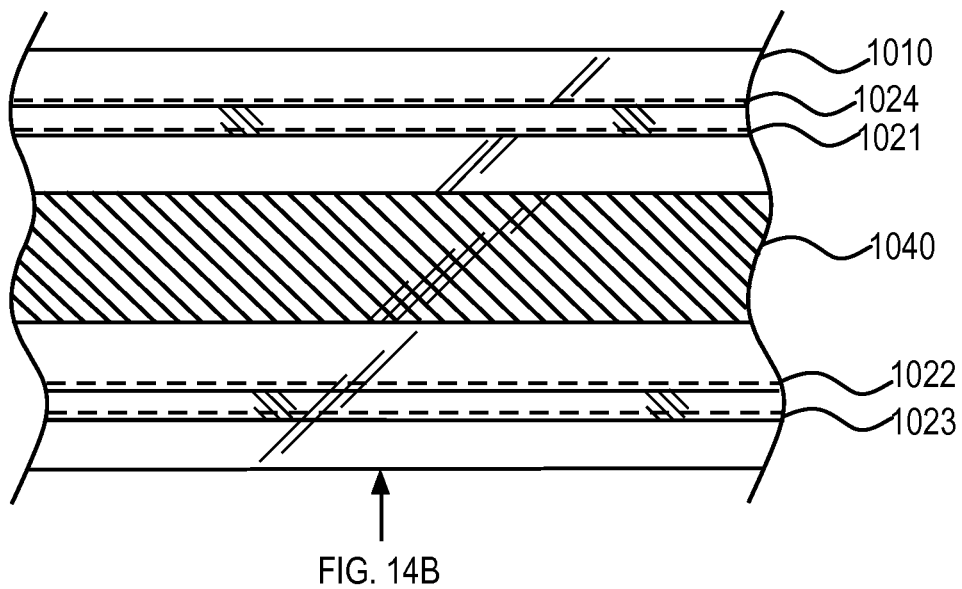
FIG. 14A is a perspective view of the catheter showing additional detail in the region of FIG. 10 that is designated "FIG. 14A," and in which the dashed lines indicate slits that are on the underside of the catheter.
Figure 14B:
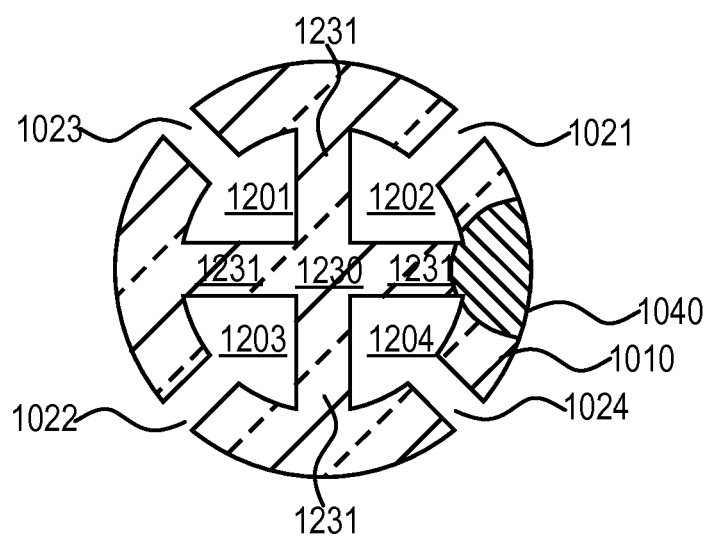
FIG. 14B is a cross-sectional view of the catheter in the region of FIG. 14A that is designated "FIG. 14B."

FIG. 14A is a perspective view of catheter 1000 showing additional detail in the region of FIG. 10 that is designated "FIG. 14A," and FIG. 14B is a cross-sectional view of catheter 1000 in the region of FIG. 14A that is designated "FIG. 14B." In this region, it may be seen that elongate member 1010 includes core portion 1230 and four septa 1231, which may be continuations of core portion 1230 and septa 1231 illustrated in FIGS. 12B-13B, and that define first, second, third, and fourth lumens 1201, 1202, 1203, 1204 that extend collinearly through elongate member 1010 and may be continuations of lumens 1201, 1202, 1203, 1204 illustrated in FIGS. 12B-13B. In this region, first slit 1021 is defined through elongate member 1010 so as to provide fluidic communication between the environment and lumen 1202, second slit 1022 is defined through elongate member 1010 so as to provide fluidic communication between the environment and lumen 1203, third slit 1023 is defined through elongate member 1010 so as to provide fluidic communication between the environment and lumen 1201, and fourth slit 1024 is defined through elongate member 1010 so as to provide fluidic communication between the environment and lumen 1204. Note that fourth slit 1024 is illustrated with broken lines to indicate that the slit is on the underside of catheter 1000.

Figure 15A:
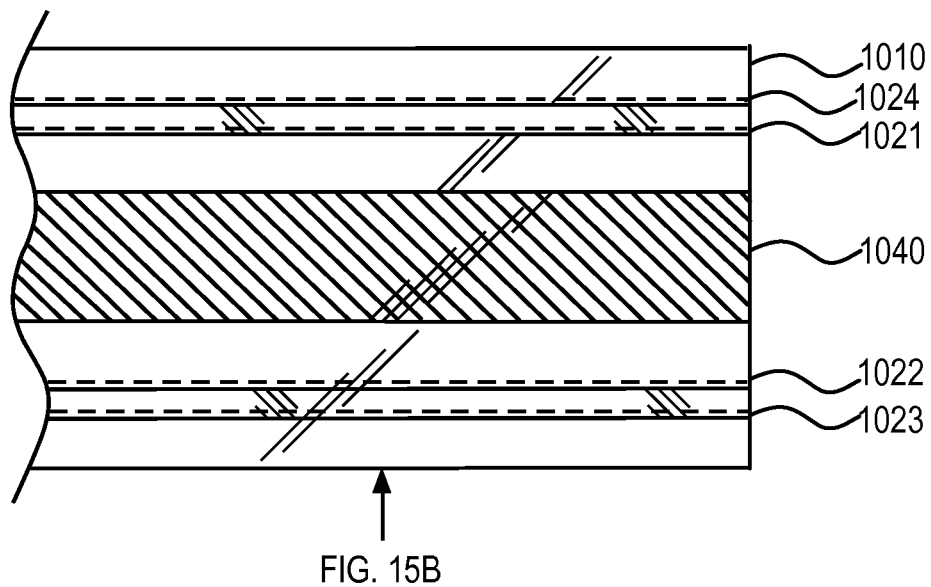
FIG. 15A is a perspective view of the catheter showing additional detail in the region of FIG. 10 that is designated "FIG. 15A," and in which the dashed lines indicate slits that are on the underside of the catheter.
Figure 15B:
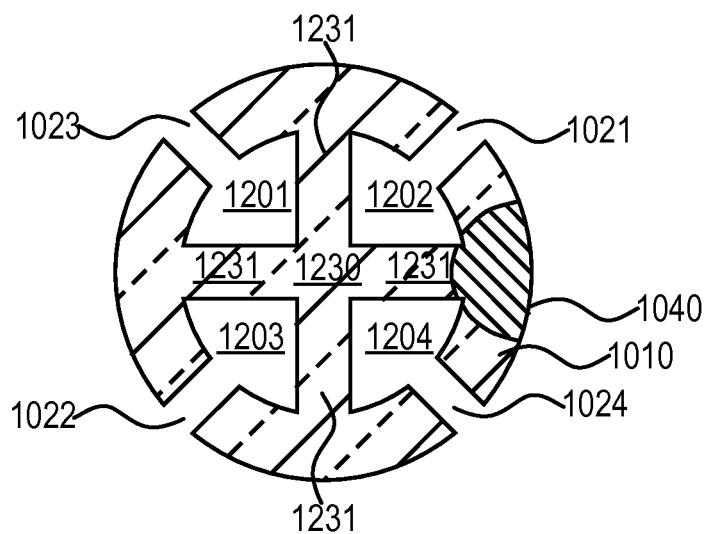
FIG. 15B is a cross-sectional view of the catheter in the region of FIG. 15A that is designated "FIG. 15B."

FIG. 15A is a perspective view of catheter 1000 showing additional detail in the region of FIG. 10 that is designated "FIG. 15A," and FIG. 15B is a cross-sectional view of catheter 1000 in the region of FIG. 15A that is designated "FIG. 15B." In this region, which includes distal end 1012 of catheter 1000, it may be seen that elongate member 1010 includes core portion 1230 and four septa 1231, which may be continuations of core portion 1230 and septa 1231 illustrated in FIGS. 12B-14B, and that define first, second, third, and fourth lumens 1201, 1202, 1203, 12404 illustrated in FIGS. 12B-14B. In this region, first slit 1021 is defined through elongate member 1010 so as to provide fluidic communication between the environment and lumen 1202, second slit 1022 is defined through elongate member 1010 so as to provide fluidic communication between the environment and lumen 1203, third slit 1023 is defined through elongate member 1010 so as to provide fluidic communication between the environment and lumen 1201, and fourth slit 1024 is defined through elongate member 1010 so as to provide fluidic communication between the environment and lumen 1204.

It will be appreciated that alternative catheter 1000 illustrated in FIGS. 10-15B suitably may be configured for peritoneal dialysis in a similar manner to catheters 200', 200" described above with reference to FIG. 2B, or for any other suitable purpose.

While various illustrative embodiments of the invention are described above, it will be apparent to one skilled in the art that various changes and modifications may be made therein without departing from the invention. For example, although use of the inventive catheters is primarily described above with reference to implantation in the peritoneal cavity, it should be understood that the inventive catheters suitably may be fully or partially implanted in any desired portion of a patient's body. Additionally, it should be noted that any desired number of lumens and staggered slits may be defined within the inventive catheters. For example, two, three, or five lumens, and a corresponding number of staggered slits, may be defined within the inventive catheters by appropriately configuring the septa and slits of the elongate member. The appended claims are intended to cover all such changes and modifications that fall within the true spirit and scope of the invention.

What is claimed:

1. A catheter, comprising:
    an elongate member;
    a plurality of septa configured to define a plurality of lumens along the elongate member; and
    a plurality of slits defined through the elongate member, each slit configured to provide fluidic communication between an environment about the catheter and a corresponding lumen of the plurality of lumens, at least one slit having a different length than at least one other slit.

2. The catheter of claim 1, wherein the plurality of septa comprises four septa configured to define four lumens along the elongate member.

3. The catheter of claim 2, wherein the plurality of slits comprise four slits.

4. The catheter of claim 3, wherein each slit of the four slits has a different length than each other slit of the four slits.

5. The catheter of claim 3, wherein two slits of the four slits have the same length as one another.

6. The catheter of claim 5, wherein the other two slits of the four slits have the same length as one another and that is different than the length of the previously mentioned two slits.

7. The catheter of claim 1, wherein the septa extend for less than the entire length of the elongate member.

8. The catheter of claim 7, wherein a proximal end of the elongate member has only a single lumen defined therethrough.

9. The catheter of claim 1, wherein the elongate member has a proximal end and a distal end, the proximal end configured to be coupled to an external device, the distal end configured to be implanted within a patient's body.

10. The catheter of claim 1, wherein the elongate member has a proximal end and a distal end, the proximal end configured to be coupled to an implantable device, the distal end configured to be implanted within a patient's body.

11. A method of using a catheter, the method comprising:
    providing a catheter comprising:

an elongate member having a proximal end and a distal end;

a plurality of septa configured to define a plurality of lumens along the elongate member; and a plurality of slits defined through the elongate member, each slit configured to provide fluidic communication between an environment about the catheter and a corresponding lumen of the plurality of lumens, at least one slit having a different length than at least one other slit; and implanting the distal end of the elongate member within a patient.

12. The catheter of claim 11, wherein the plurality of septa comprises four septa configured to define four lumens along the elongate member.

13. The catheter of claim 12, wherein the plurality of slits comprise four slits.

14. The catheter of claim 13, wherein each slit of the four slits has a different length than each other slit of the four slits.

15. The catheter of claim 13, wherein two slits of the four slits have the same length as one another.

16. The catheter of claim 15, wherein the other two slits of the four slits have the same length as one another and that is different than the length of the previously mentioned two slits.

17. The catheter of claim 11, wherein the septa extend for less than the entire length of the elongate member.

18. The catheter of claim 17, wherein a proximal end of the elongate member has only a single lumen defined therethrough.

19. The catheter of claim 11, further comprising coupling the proximal end of the elongate member to a device external to the patient's body.

20. The catheter of claim 11, further comprising coupling the proximal end of the elongate member to a device implantable within the patient's body.

* * * * *